United States Patent [19]

Kobzina

[11] 4,244,730

[45] Jan. 13, 1981

[54] HERBICIDAL N-HALOACETYL-2-ALKYL-6-ACYLANI-LINES

[75] Inventor: John W. Kobzina, Walnut Creek, Calif.

[73] Assignee: Chevron Research Company, San Francisco, Calif.

[21] Appl. No.: 53,877

[22] Filed: Jul. 2, 1979

[51] Int. Cl.³ .................... A01N 43/30; A01N 43/32
[52] U.S. Cl. .......................................... 71/88; 71/98; 71/118; 260/338; 260/340.7; 260/340.9 R; 564/74; 564/212; 564/214
[58] Field of Search ................. 71/88, 98, 118; 260/338, 340.7, 340.9 R

[56] References Cited

U.S. PATENT DOCUMENTS

| | | | |
|---|---|---|---|
| 3,739,024 | 6/1973 | Chupp | 71/98 |
| 4,053,297 | 10/1977 | Richter | 71/118 |
| 4,146,387 | 3/1979 | Thiele | 71/118 |
| 4,168,965 | 9/1979 | Vogel et al. | 71/118 |

*Primary Examiner*—Paul M. Coughlan, Jr.
*Attorney, Agent, or Firm*—D. A. Newell; T. G. DeJonghe; R. J. Suyat

[57] ABSTRACT

Compounds of the formula

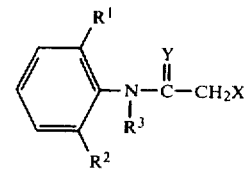

wherein $R^1$ is alkyl or alkoxy; $R^2$ is substituted alkly or substituted alkenly containing 1 or 2 hydroxy or alkoxy substituents, acyl, and ketal group of the formula

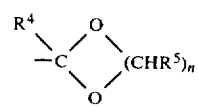

wherein $n = 2$, 3 or 4, $R^4$ is alkyl and $R^5$ is hydrogen or alkyl, an oxime of the formula

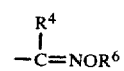

wherein $R^6$ is hydrogen or alkyl; $R^3$ is hydrogen or alkyl; X is halo and Y is oxygen or sulfur have herbicidal activity.

7 Claims, No Drawings

HERBICIDAL N-HALOACETYL-2-ALKYL-6-ACYLANILINES

BACKGROUND OF THE INVENTION

U.S. Pat. No. 4,141,989 discloses 3-(N-chloroacetyl(-N-2,6-dialklyphenylamino)-gamma-butyrolactones) as fungicides.

U.S. Pat. No. 4,055,410 discloses substituted bromo and chloroacetamides as herbicides.

SUMMARY OF THE INVENTION

This invention relates to novel N-haloacetyl-2-alkyl-6-acylaniline compounds, methods of their use as herbicides and herbicidal compositions thereof. It has now been found that the placement of certain acyl, ketal, oxime, hydroxyalkyl and alkoxyalkyl substituents on the 6-position of N-haloacetyl-2-alkyl anilines results in compounds having herbicidal activity. The compounds of the invention are particularly effective for pre-emergent treatment of grassy weeds.

DESCRIPTION OF THE INVENTION

The compounds of the invention are represented by the formula:

(I)

wherein $R^1$ is alkyl of 1 to 4 carbon atoms; or alkoxy of 1 to 4 carbon atoms;

$R^2$ is substituted alkyl of 1 to 6 carbon atoms or substituted alkenyl of 1 to 6 carbon atoms substituted with 1 or 2 hydroxy groups or 1 or 2 alkoxy groups of 1 to 3 carbon atoms; acyl of 2 to 4 carbon atoms; a group of the formula wherein n=2, 3 or 4; $R^4$ is alkyl of 1 to 3 carbon atoms and $R^5$ is hydrogen or alkyl of 1 to 3 carbon atoms; a group of the formula $$-\overset{R^4}{\underset{|}{C}}=NOR^6$$

wherein $R^4$ is defined above and $R^6$ is hydrogen or alkyl of 1 to 3 carbon atoms $R^3$ is hydrogen or alkyl of 1 to 4 carbon atoms; X is halogen; and Y is oxygen or sulfur.

Representative $R^1$ groups are methyl, ethyl, n-propyl, i-propyl, methoxy, ethoxy and i-propoxy. Preferably $R^1$ is methyl.

Representative substituted alkyl and acyl $R^2$ groups are 1-hydroxyethyl, 1,2-bis-methoxyethyl, acetyl and propionyl.

Representative ketal $R^2$ groups are

Representative oxime $R^2$ groups are $$-\underset{|}{\overset{CH_3}{C}}=NOCH_2CH_3, -\underset{|}{\overset{CH_3}{C}}=NOCH_3, -\underset{|}{\overset{CH_3}{C}}=NOH,$$

$$-\underset{\overset{|}{CH_2CH_3}}{\overset{|}{C}}=NOCH_2CH_3, -\underset{\overset{|}{CH_2CH_3}}{\overset{|}{C}}=NOCH_3, -\underset{\overset{|}{CH_2CH_3}}{\overset{|}{C}}=NOH.$$

Representative $R^3$ groups are hydrogen, methyl, ethyl, i-propyl, n-propyl, n-butyl, i-butyl.

Preferably $R^2$ is $-\underset{|}{\overset{CH_3}{C}}=NOCH_2CH_3$ or

. Most preferred is

. Preferably $R^3$ is hydrogen.

Representative X groups are chloro, bromo, fluoro, iodo. Preferably X is chloro. Preferably Y is oxygen.

The compounds of the invention may be made according to the following scheme.

(1)

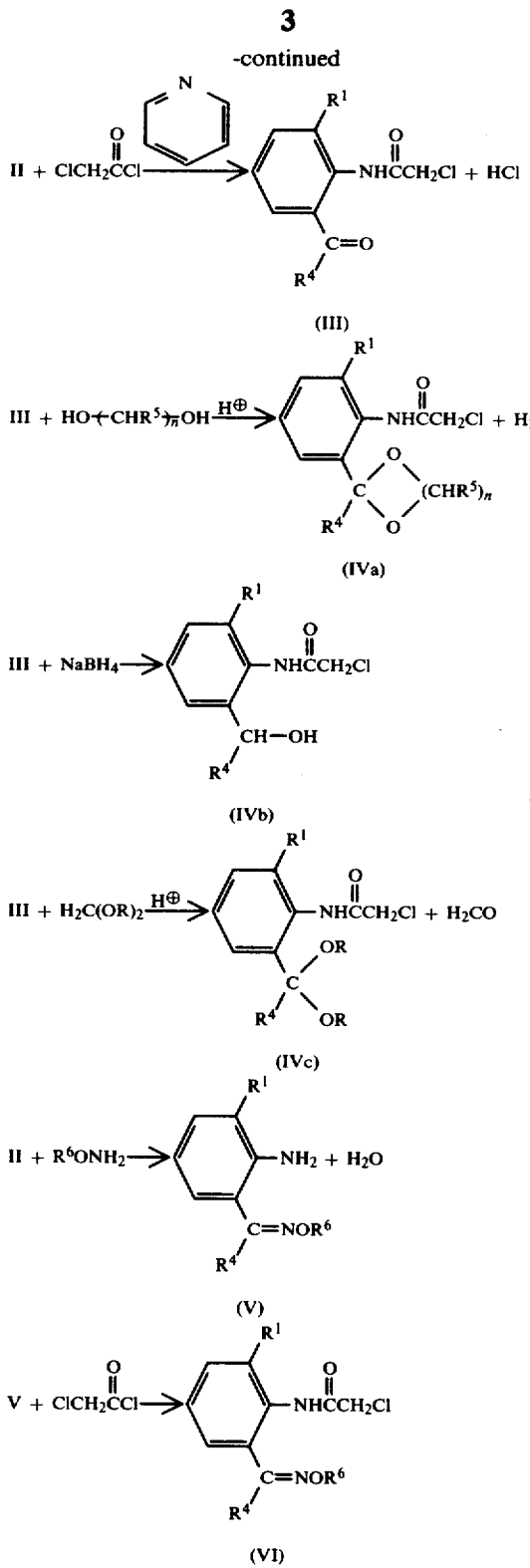

The above reactions are conventional deacetylation (1), acetylation (2 and 5), ketalization (3a and 3c) and reduction (3b) reactions and may be performed by known procedures. Reaction (4) is generally conducted by reacting substantially equimolor amounts of the carbonyl compound (II) and the alkoxyamine in the liquid phase in an inert diluent at a temperature of 0° to 100° C. Generally, the alkoxyamine is generated in situ from the corresponding alkoxyamino hydrochloride or methoxyamine hydrochloride, and a base, e.g., an inorganic alkali metal carbonate such as potassium carbonate or a trialkyl amine such as triethylamine.

The compounds of the present invention are, in general, herbicidal in both pre- and post-emergent applications, but are particularly effective in pre-emergent applications. For pre-emergent control of undesirable vegetation, the herbicidal compounds will be applied in herbicidally effective amounts to the locus or growth medium of the vegetation, e.g. soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broad-leaved weeds. Some may be selective with respect to the type of application and/or type of weed. The compounds of the invention are particularly effective as pre-emergent herbicides against weed grasses.

The compounds, when applied to growing plants above the ground in such an amount that the compounds will not kill beneficial plants, also show efficient plant growth regulating or retarding effects and may be advantageously employed, for example, to prevent or retard the growth of lateral buds in plants and to promote the thinning out of superfluous fruits in various fruit trees.

The compounds can be applied in any of a variety of compositions. In general, the compounds can be extended with a carrier material of the kind used and commonly referred to in the art such as inert solids, water and organic liquids.

The compounds will be included in such compositions in sufficient amount so that they can exert an herbicidal or growth-regulating effect. Usually from about 0.5 to 95% by weight of the compounds are included in such formulations.

Solid compositions can be made with inert powders. The compositions thus can be homogeneous powders that can be used as such, diluted with inert solids to form dusts, or suspended in a suitable liquid medium for spray application. The powders usually comprise the active ingredient admixed with minor amounts of conditioning agent. Natural clays, either absorptive, such as attapulgite, or relatively non-absorptive, such as china clays, diatomaceous earth, synthetic fine silica, calcium silicate and other inert solid carriers of the kind conventionally employed in powdered herbicidal compositions can be used. The active ingredient usually makes up from 0.5–90% of these powder compositions. The solids ordinarily should be very finely divided. For conversion of the powders to dusts, talc, pyrophyllite, and the like, are customarily used.

Liquid compositions including the active compounds described above can be prepared by admixing the compound with a suitable liquid diluent medium. Typical of the liquid media commonly employed are methanol, benezene, toluene, and the like. The active ingredient usually makes up from about 0.5 to 50% of these liquid compositions. Some of these compositions are designated to be used as such, and others to be extended with large quantities of water.

Compositions in the form of wettable powders or liquids can also include one or more surface-active agents, such as wetting, dispersing or emulsifying agents. The surface-active agents cause the compositions of wettable powders or liquids to disperse or emulsify easily in water to give aqueous sprays.

The surface-active agents employed can be of the anionic, cationic or nonionic type. They include, or example, sodium long-chain carboxylates, alkyl aryl sulfonates, sodium lauryl sulfate, polyethylene oxides, lignin sulfonates and other surface-active agents.

When used as a pre-emergent treatment, it is desirable to include a fertilizer, an insecticide, a fungicide or another herbicide.

The amount of compound or composition administered will vary with the particular plant part or plant growth medium which is to be contacted, the general location of application—i.e., sheltered areas such as greenhouses, as compared to exposed areas such as fields—as well as the desired type of control. Generally for both pre- and post-emergent herbicidal control, the compounds of the invention are applied at rates of 0.2 to 60 kg/ha, and the preferred rate is in the range 0.5 to 40 kg/ha. For plant growth regulating or retarding activity, it is essential to apply the oxime compounds at a concentration not so high as to kill the plants. Therefore, the application rates for plant growth regulating or retarding activity will generally be lower than the rates used for killing the plants. Generally, such rates vary from 0.1 to 5 kg/ha, and preferably from 0.1 to 3 kg/ha.

Herbicidal tests on representative compounds of the invention were made using the following methods.

Pre-Emergent Herbicidal Test

An acetone solution of the test compound was prepared by mixing 375 mg of the compound, 118 mg of a nonionic surfactant and 18 ml of acetone. 10 ml of this solution was added to 40 ml of water to give the test solution.

Seeds of the test vegetation were planted in a pot of soil and the test solution was sprayed uniformly onto the soil surface at a dose of 27.5 micrograms/cm$^2$. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table I.

Post-Emergent Herbicidal Test

The test compound was formulated in the same manner as described above for the pre-emergent test. This formulation was uniformly sprayed on 2 similar pots of 24-day-old plants (approximately 15 to 25 plants per pot) at a dose of 27.5 microgram/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table I.

EXAMPLE 1

Preparation of N-Chloroacetyl-2-methyl-6-acetylaniline

A. N-Acetyl-2-methyl-6-acetylaniline (76.1 g) in water (300 ml), ethanol (300 ml), concentrated hydrochloric acid (300 ml) and concentrated sulfuric acid (15 ml) were refluxed for 24 hours. The solution was cooled and concentrated ammonium hydroxide was added to pH 10. The solution was extracted with dichloromethane. The extracts were dried (MgSO$_4$) and stripped. 2-methyl-6-acetylaniline (49.3 g) was obtained as a tan solid.

B. 2-Methyl-6-acetylaniline (25 g) and pyridine (26.5 g) in 1 liter methylene chloride were cooled in an ice-acetone bath. A solution of chloroacetyl chloride (37.9 g) in 100 ml methylene chloride was dripped in slowly. The solution was stirred at room temperature for 2 hours, washed with 10% HCl, 10% NaOH, dried (MgSO$_4$) and stripped. Yield: the title product as a white solid, MP 88°–89° C.

EXAMPLE 2

Preparation of 2,4,5-Trimethyl-2-(3-methyl-2-chloroacetamidophenyl)dioxolane

The product from Example 1 (10.6 g), 2,3-dihydroxybutane (8.5 g) and p-toluene sulfonic acid (1.5 g) in 200 ml benzene were refluxed to 2 hours, removing water with a Dean-Stark trap. The solution wash washed with 10% NaOH, dried (MgSO$_4$) and stripped. The product was chromatographed on a silica gel column, eluting with 30% ether-hexane. Yield: 3.8 g of the title product, mp 55°–57° C.

EXAMPLE 3

Preparation of (3'-methyl-2'-chloroacetamido) acetophenone O-methyloxime

2-Methyl-6-acetylaniline (from Example 1A) was refluxed with methoxyamine hydrochloride in ethanol to yield (3'-methyl-2'-amino) acetophenone O-methyl oxime (I).

Compound I (1.72 g) and 1 g triethylamine in 35 ml methylene chloride were cooled in an ice bath and 1.1 g chloroacetyl chloride was added slowly.

The solution was stirred at room temperature overnight, washed with 10% HCl, 10% NaHCO$_3$, water and dried (MgSO$_4$). The solvent was stripped to yield 1.2 g of the title product, m.p. 119°–120° C.

TABLE A

Compounds of the Formula $$\underset{R^2\;R^3}{\underset{|}{\underset{R^1}{}}}\text{Ar-N-C(O)CH}_2\text{Cl}$$

(2,6-disubstituted phenyl with N-R³ bearing C(O)CH₂Cl group)

| No. | R¹ | R³ | R² | m.p. °C. | C CAL. | C FD. | H CAL. | H FD. | N CAL. | N FD. |
|---|---|---|---|---|---|---|---|---|---|---|
| 1 | CH₃ | H | –C(CH₃)(O–CH₂CH₂–O) (1,3-dioxolan-2-yl, 2-methyl) | oil | 13.1[a] | 11.7[a] | | | | |
| 2 | C₂H₅ | H | –C(CH₃)(O–CH₂CH₂–O) | 87–91 | 59.25 | 53.39 | 6.40 | 6.37 | 4.94 | 5.01 |
| 3 | C₂H₅ | H | –C(CH₃)(O–CH₂CH₂CH₂–O) (1,3-dioxan-2-yl, 2-methyl) | oil | 60.50 | 58.76 | 6.77 | 6.37 | 4.70 | 5.01 |
| 4 | CH(CH₃)₂ | H | –C(CH₃)(O–CH₂CH₂–O) | 97–98 | 60.50 | 55.1 | 6.77 | 5.89 | 4.70 | 4.34 |
| 5 | CH₃ | H | –C(CH₃)=NOC₂H₅ | 86–87 | 13.2[a] | 16.1[a] | | | | |
| 6 | CH₃ | H | –C(CH₃)(O–CH(CH₃)CH(CH₃)–O) | 55–57 | 60.50 | 58.94 | 6.77 | 6.63 | 4.70 | 4.58 |
| 7 | CH(CH₃)₂ | H | –C(CH₃)(O–CH(CH₃)CH(CH₃)–O) | 67–68 | 62.66 | 63.44 | 7.42 | 7.53 | 4.30 | 4.4 |
| 8 | C₂H₅ | H | –C(CH₃)(O–CH(CH₃)CH(CH₃)–O) | 72–74 | 61.62 | 62.51 | 7.11 | 7.24 | 4.49 | 4.48 |
| 9 | CH₃ | H | –C(OCH₃)₂CH₃ | oil | 57.45 | 59.92 | 6.68 | 6.47 | 5.16 | 5.27 |
| 10 | CH₃ | H | –C(CH₃)=NOCH₃ | 119–120 | 56.58 | 56.85 | 5.94 | 6.16 | 11.0 | 11.24 |
| 11 | CH(CH₃)₂ | H | –C(CH₃)=NOCH₃ | 108–110 | 59.46 | 60.62 | 6.77 | 6.82 | 9.91 | 9.53 |
| 12 | CH₃ | C₂H₅ | –C(OCH₃)₂CH₃ | 61–64 | 60.09 | 59.21 | 7.40 | 7.33 | 4.67 | 4.48 |
| 13 | CH₃ | C₂H₅ | –C(=CH₂)OCH₃ | oil | 62.80 | 61.44 | 6.78 | 6.96 | 5.23 | 4.87 |
| 14 | CH₃ | H | –C(O)C₂H₅ | 75–77 | 60.13 | 59.76 | 5.89 | 6.05 | 5.84 | 5.69 |
| 15 | CH₃ | C₂H₅ | –C(O)CH₃ | oil | 61.53 | 59.07 | 6.36 | 6.08 | 5.52 | 5.12 |
| 16 | CH₃ | H | –CH(CH₃)OH | 77–79 | 58.02 | 55.7 | 6.20 | 6.14 | 6.15 | 6.0 |
| 17 | C₂H₅ | H | –CH(CH₃)OH | 113–114 | 59.62 | 58.89 | 6.67 | 6.75 | 5.80 | 6.0 |
| 18 | CH₃ | H | –C(O)CH₃ | 88–89 | 58.54 | 54.53 | 5.36 | 4.95 | 6.21 | 5.7 |

TABLE A-continued

Compounds of the Formula

| No. | R¹ | R³ | R² | m.p. °C. | C CAL. | C FD. | H CAL. | H FD. | N CAL. | N FD. |
|---|---|---|---|---|---|---|---|---|---|---|
| 19 | CH(CH₃)₂ | H | —C(=O)CH₃ | 118–120 | 61.53 | 56.71 | 6.36 | 5.59 | 5.52 | 4.29 |

ᵃChlorine

TABLE I

HERBICIDAL ACTIVITY

Pre/Post % Control

| No. | L | M | P | C | W | O |
|---|---|---|---|---|---|---|
| 1 | 65/60 | 60/60 | 75/20 | 97/60 | 100/60 | 99/15 |
| 2 | 55/0 | 55/0 | 60/0 | 100/20 | 100/45 | 98/20 |
| 3 | 0/0 | 0/0 | 0/0 | 90/0 | 90/0 | 55/0 |
| 4 | 0/0 | 0/0 | 0/0 | 90/0 | 90/0 | 50/0 |
| 5 | 10/0 | 0/0 | 0/0 | 95/0 | 100/0 | 70/0 |
| 6 | 50/0 | 78/0 | 95/0 | 100/65 | 100/85 | 98/20 |
| 7 | 0/0 | 30/0 | 0/0 | 92/0 | 95/30 | 90/10 |
| 8 | 45/0 | 82/0 | 85/0 | 100/55 | 100/85 | 95/20 |
| 9 | 0/0 | 0/0 | 0/0 | 100/0 | 90/0 | 15/0 |
| 10 | 40/0 | 30/0 | 60/0 | 95/0 | 100/60 | 15/0 |
| 11 | 0/0 | 0/0 | 0/0 | 90/0 | 95/0 | 0/0 |
| 12 | 0/30 | 0/20 | 0/25 | 95/15 | 97/15 | 30/0 |
| 13 | 0/15 | 0/10 | 0/0 | 90/40 | 95/50 | 40/20 |
| 14 | 10/55 | 10/45 | 25/65 | 100/50 | 100/50 | 97/15 |
| 15 | 0/0 | 0/0 | 0/0 | 97/55 | 95/30 | 25/0 |
| 16 | 0/0 | 0/0 | 0/0 | 75/0 | 80/0 | 0/0 |
| 17 | 0/0 | 0/0 | 0/0 | 90/0 | 95/0 | 15/0 |
| 18 | 0/0 | 0/0 | 0/0 | 98/0 | 95/0 | 0/0 |
| 19 | 0/0 | 0/0 | 0/0 | 80/0 | 85/0 | 20/0 |

L = Lambsquarter (*Chenopodium album*)
M = Mustard (*Brassica arvensis*)
P = Pigweed (*Amaranthus retroflexus*)
C = Crabgrass (*Digitaria sanquinalis*)
W = Watergrass (*Echinochola crusgalli*)
O = Wild Oats (*Avenua fatua*)

What is claimed is:

1. A compound of the formula

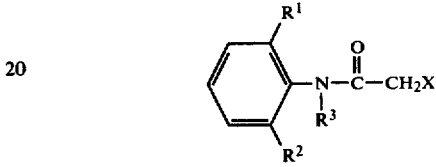

wherein R¹ is alkyl of 1 to 4 carbon atoms; or alkoxy of 1 to 4 carbon atoms; R² is a group of the formula

wherein n=2, 3 or 4; R⁴ is alkyl of 1 to 3 carbon atoms and R⁵ is hydrogen or alkyl of 1 to 3 carbon atoms; R³ is hydrogen or alkyl of 1 to 4 carbon atoms; and X is halogen.

2. A compound according to claim 1 wherein X is chloro.

3. A compound according to claim 2 wherein R¹ is methyl, R³ is hydrogen, R⁴ and R⁵ are methyl and n is 2.

4. An herbicidal composition comprising a biologically inert carrier and an herbicidally effective amount of the compound of the formula defined in claim 1.

5. A method for killing vegetation which comprises applying to said vegetation or its growth environment an herbicidally effective amount of the compound of the formula defined in claim 1.

6. An herbicidal composition comprising a biologically inert carrier and an herbicidally effective amount of the compound of the formula defined in claim 3.

7. A method for killing vegetation which comprises applying to said vegetation or its growth environment an herbicidally effective amount of the compound of the formula defined in claim 3.

* * * * *